United States Patent [19]
Gennari et al.

[11] Patent Number: 5,869,725
[45] Date of Patent: Feb. 9, 1999

[54] DERIVATIVES OF AMINOSULFONIC ACIDS, UTILIZATION OF THE SAME IN THE SYNTHESIS OF PSEUDOPEPTIDES AND PROCESS FOR THEIR PREPARATION

[75] Inventors: Cesare Gennari; Donatella Potenza, both of Milan; Barbara Salom, Vedano Al Lambro-Me, all of Italy

[73] Assignee: Pharmacia & UpJohn S.P.A., Milan, Italy

[21] Appl. No.: 737,379

[22] PCT Filed: May 11, 1995

[86] PCT No.: PCT/EP95/01788

§ 371 Date: Oct. 30, 1996

§ 102(e) Date: Oct. 30, 1996

[87] PCT Pub. No.: WO95/31433

PCT Pub. Date: Nov. 23, 1995

[30] Foreign Application Priority Data

May 17, 1994 [IT] Italy ............................ MI94 A 000989

[51] Int. Cl.$^6$ ............................ C07F 7/18; C07C 311/47; C07C 311/34; C07C 309/83
[52] U.S. Cl. ............................ 556/420; 558/48; 558/49; 558/50; 560/148; 562/104; 562/105; 562/106; 564/82; 564/86; 564/95
[58] Field of Search ............................ 556/420; 558/48, 558/49, 50; 560/150, 148; 564/82, 95; 562/104, 105

[56] References Cited

PUBLICATIONS

Marchand–Brynaert, J. et al. Isreal J. Chem., 29, 247 (1989).
Gennari, Cesare et al. Angnew. Chem., 106(20), 2181–2183 (1994).
Gilmore W.F. et al., J. Org. Chem. 43, 4535 (1978). Synthesis of carbamates of alfa–amino sulfonamides
Moe G.R. et al., Tetrahedron Letters 22, 537 (1981) An explanation for the failure of aminomethanesulfonic acid to form sulfonamides . . . .
Garrigues B. et al., Synthesis 810 (1988) Salts of N–alkyl-sulfonated ureas and thioureas.
Gilmore W.F. et al., J. Org. Chem. 43, 4535 ((2978) Synthesis of carbamates of alfa–amio sulfonamides.
Moe G.R. et al., Tetrahedron Letters 22, 537 (1981) An explanation for the failure of aminoethanesulfonic acid to form sulfonamides . . . .
Garrigues B. et al., Synthesis 810 (1988) Salts of N–alkyl-sulfonated ureas and thioureas.
Reyna et al., Proc.Natl.Sci., USA, 89?9367 (1992) Peptoids: A modular approach to drug discovery.
Schreiber et al., Jacs 114, 6570 (1992) Reassignment of stereochemistry and total synthesis of the thrombin inhibitor cyclotheonamide B.
Schreiber et al., Jacs 115, 12619 (1993) Atomic structure of the trypsin–cyclotheonamide A Complex: lessons for the design of serine protease inhibit.
L. Ghosez et al., Bull.Soc.Chim.Fr (1990)127, 835–842. Synthesis of alfa, β–Epoxysulfonic acids as potential inhibitors of bacterial D, D–Peptidases.
V. du Vigneaud et al., J.Am.Chem.Soc. 75,4879 (1953) The Synthesis of an Octapeptide Amide with the Hormonal Activity of Oxytocin.
R.Huguenin et al., Helv.Chim.Acta 49,695 (1966) Synthese de la Desamino–Arg–Vasopressine Et De La Desamino Phe–Arg–Vasopressine, Deux Analogues Possedant Une . . . .
R.Hirschmann, Angew.Chem.Int.Ed.Engl. 30, 1278–1301 (1991) Medicinal Chemistry in the golden age of biology: lessons from steroid and peptide research.
D.B. Sherman et al., J.Am.Chem.Soc. 112, 433–411 (1990) Compatibility of thioamides with reverse turn features: synthesis and conformational . . . .
Moree W.J. et al., Tetrahedron Letters 33, 6389 (1992) Synthesis of peptides containing the β–substituted aminoethane sulfinamide or sulfonamide transition state . . . .
Kricheldorf, H.R. et al., Synthesis 43 (1976) Synthese von peptiden des taurins und der sulfanilsaure.
Luisi G. et al., Tetrahedron Letters 34, 2391 (1993) ps(SO2–NH) transition state isosteres of peptides. Synthesis of the glutathione disulfide analogue . . . .
Levenson C.H., J.Med.Chem. 27, 228 (1984) Design and synthesis of tetrahedral intermediate analogues as potential dihydroorotase inhibitors.
Guegan R. et al., J.Med.Chem. 29, 1152 (1986) Pepstatin analogues as novel renin inhibitors.
Mazdiyasni H. et al., Tetrahedron Letters 34, 435 (1993) Enzyme catalyzed synthesis of optically pure β–sulfonamido propionic acids. Useful starting materials for P–3 . . .
Frankel et al., Tetrahedron 9, 289 (1960) Syntheses of amino alkyl sulphonic acids and their peptide analogues.
Merriks D. et al, J.Chem.Soc., Perkin 1, 2169 (1991) Some studies on peptide analogues involving the sulphinamide group.
Vavra I. et al., The Lancet, May 4, 1968, 948 Effect of a synthetic analogue of vasopressin in animals and in . . . .

*Primary Examiner*—Michael G. Ambrose
*Attorney, Agent, or Firm*—Collard & Roe, P.C.

[57] ABSTRACT

Derivatives of gamma-amino-alpha,beta-unsaturated sulfonic acids, a process for the preparation of the same and their utilization in the synthesis of pseudopeptides characterized by the presence of at least a sulfonamide type bond conjugated to a double bond are described.

10 Claims, No Drawings

DERIVATIVES OF AMINOSULFONIC ACIDS, UTILIZATION OF THE SAME IN THE SYNTHESIS OF PSEUDOPEPTIDES AND PROCESS FOR THEIR PREPARATION

BACKGROUND OF THE INVENTION

This invention relates to derivatives of aminosulfonic acids and the utilization of the same in the synthesis of pseudopeptides characterized by the presence of at least a sulfonamide type bond, and having a potential pharmacological activity. This invention relates also to a process for the synthesis of said derivatives of aminosulfonic acids as well as their utilization in the synthesis of said pseudopeptides.

STATE OF THE ART

As is known, peptides have been studied for a long time, as they are the transition term in the study of more complex substances such as proteins; besides, peptides as such are already extremely important compounds, being the mediators of biological systems and having proved to be of great importance in the physiological and medical sectors.

Thanks to their characteristics, peptides develop in the nature a basic biological role, and are in many cases drugs to be used in several pathological conditions. In this relation, many studies have been carried out since the fifties to determine the structure of many biologically active peptides; the determination of the structures has allowed to set up the synthesis of the peptides under examination and therefore to study their potential therapeutic effects.

In many cases, such studies have led to satisfactory results, and in the years it was possibile to determine the structure, and consequently, to synthesize many peptides and proteins having a pharmacological activity. One of the more important results achieved in this field was the determination of the whole series of aminoacids and the synthesis of insulin; other studies concerned, for instance, glutathione, a tripeptide which is found in the majority of living cells, alpha-corticotropin, which is composed by 39 aminoacids and is a component of the adrenocorticotrophic hormone ACTH, and oxytocin, a nonapeptide, which is a hormone of the hypophysis involved in the contractions of the uterus; the latter peptide, after long studies, has been isolated, characterized and synthesized, as reported in V. du VIGNEAUD, C.RESSLER, J.M.SWAN, C. W. ROBERTS, P. G. KATSOYANNIS, S. GORDON, J.Am.Chem.Soc. 75,4879 (1953). Thanks to such studies, this substance is today a real drug which is normally used during delivery to induce contractions. Of clinical interest is also an analogous of vasopressin, constituted by eight aminoacids and synthesized by R. HUGUENIN et al., Helv.Chim.Acta 49,695 (1966) and I. VAVRA et al., Lancet 1,948 (1968), which proved to be a powerful and selective antidiuretic to be used in the treatment of diabetes insipidus.

Other peptides analogous of vasopressin have been synthesized, which have also shown an antiduretic activity and have proven useful in promoting an increase in blood pressure.

As is known, the structure of peptides is characterized by the presence of amide bonds which are also indicated by the term of peptide bonds; such bonds have the great drawback of being easily hydrolyzable by hydrolytic enzymes (proteases) which recognize them. The above hydrolytic activity by the enzymes causes the breakdown of the molecule into fragments of different lengths, generally devoided of the pharmacological activity which characterizes the starting peptide.

Hence, it is evident that the utilization of peptides as drugs involves the serious drawback that in the majority of cases the molecule provided with pharmacological activity does not reach the target where said pharmacological activity should be exercized as, as soon as it enters the circle, it is attacked by the hydrolytic enzymes, and because of the hydrolysis of some peptide bonds that has taken place, it is reduced into many fragments almost always devoided of any pharmacological activity. Besides, peptides show generally a low or non-existent oral bioavailability, with the ensuing administration problems.

To obviate the aforementioned drawbacks, many studies have been carried out suitable to identify compounds having structures and characteristics similar to those of peptides, in order to preserve the pharmacological activity, but characterized in that one or more peptide bonds, responsible for the already described instability of the peptide molecules because of their degradation in lower fragments, are replaced by bonds of a different type.

For instance, there have been described by REYNA J. SIMON et al. of the Chiron Corp. [Proc.Natl.Acad.Sci., USA, 89,9367 (1992)] the so-called "peptoids", compounds which contain in their structure the same side chains as those of natural aminoacids, but which come from the bond between several molecules of N-substituted glycine; as a consequence, as they lack the amide bonds characteristic of natural peptides, as shown in the following formulae, they are resistant against enzymatic degradation and are potentially utilizable as "peptidomimetic" drugs.

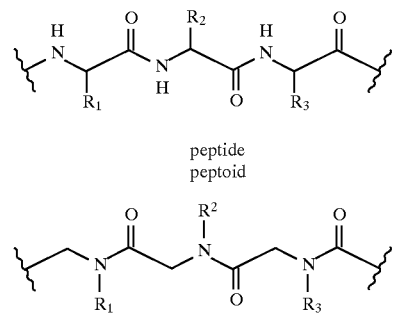

peptide
peptoid

Other methods utilized for the synthesis of "peptidomimetic" compounds use the so-called vinylog aminoacids in the construction of the prefixed sequence; as reported, for instance, by C&EN, Sep. 20, 1993, p. 34, a vynilog aminoacid is a compound where an ethylene group (i.e. two carbon atoms united by a double bond) is inserted between the carbon atom in alpha position and the carbonylic carbon atom of a conventional aminoacid. A vinylog aminoacid (Tirosina viniloga) is, for instance, a component of a cyclic peptide, the cyclotheonamide, a thrombin inhibitor [SCHREIBER S. L. et al.

JACS 114,6570 (1992); SCHREIBER et al. JACS 115, 12619 (1993)].

The utilization of vinylog aminoacids in the synthesis of peptidomimetics lends the compounds obtained special chemical-physical and conformation characteristics that may induce, for instance, a different and more marked pharmacological activity compared with the corresponding traditional peptides, but that does not solve the already mentioned problem of the hydrolysis of the peptide bond which is present also in the so obtained peptidomimetics.

Always with the purpose of obviating the aforementioned drawbacks, many research groups throughout the world have studied the possibility of substituting at least an amide bond within the peptide structure with bonds having similar characteristics but that are no longer recognizable by the hydrolytic enzymes, trying in this way to cause the molecule to be less sensitive to hydrolysis, while keeping at the same time unaltered as much as possible the sequence of natural aminoacids which constitute the peptide, in order to preserve its characteristic pharmacological activity. This type of approach is known as "isosteric substitution" of the peptide bond and consists, for instance, in the substitution of such peptide bond (—CO—NH—) with groups such as ketomethylene isosters (—CO—CH$_2$—), amines (—CH$_2$—NH—), ethylene bonds (—CH=CH—), alpha-difluoroketones (CO—CF$_2$—), cyclopropane isosters and the like [Angew.Chem.Int.Ed.Engl. 30, 1278–1301 (1991)]. The aforementioned approach has allowed to obtain "pseudopeptide" compounds having a significantly higher biostability, even though such substitutions of the amide bond have caused in the pseudopeptides so obtained solubility and administration problems. A particular attempt of isosteric substitution is reported by D. B. SHERMAN, A. F. SPATOLA, J.Am.Chem.Soc. 112,433–441 (1990) who, to perform such substitution, have utilized a thioamide bond (—CS—NH—) which differs from the peptide one (—CO—NH—) because of the substitution of amide oxygen with sulphur; unfortunately, although thioamides mimic amides satisfactorily, the biological studies carried out on these pseudopeptides have shown that the biological behaviour of the compounds containing thioamide bonds is unforeseenable. Always in the field of isosteric substitution of the peptide bond, pseudopeptides have also been studied characterized by the presence of at least a sulfonamide bond substituting for an amide bond [MOREE, W. J. et al. Tetrahedron Letters 33,6389 (1992); KRICHELDORF, H. R. et al. Synthesis 43 (1976); LUISI, G. et al. Tetrahedron Letters 34,2391 (1993)]; this change creates a surrogate of the peptide bond which results to be characterized by significant changes in the polarity, the capacity of producing hydrogen bonds, and the acid-base character of the molecule.

Besides, the sulfonamide bond shows a greater metabolic stability compared with the amide bond, and is structurally similar to the tetraedric transition state involved in the enzymatic hydrolysis of the amide bond, causing the pseudopeptides containing at least a sulfonamide bond to become interesting candidates in the development of enzymatic inhibitors and new drugs [LEVENSON, C. H. et al. J.Med.Chem. 27,228 (1984); GUEGAN, R. et al. J.Med.Chem. 29,1152 (1986); MAZDIYASNI, H. et al. Tetrahedron Letters 34,435 (1993)]. To obtain pseudopeptides characterized by the presence of at least a sulfonamide bond, it has been tried to use alpha-aminosulfonamides, which however are known to be unstable and to decompose immediately by fragmentation [FRANKEL, M. et al. Tetrahedron 9,289 (1960); GILMORE, W. F. et al. J.Org.Chem. 43,4535 (1978); MOE, G. R. et al. Tetrahedron Letters 22,537 (1981); GARRIGUES, B. et al. Synthesis 810 (1988); MERRICKS, D. et al. J.Chem. Soc., Perkin 1, 2169 (1991)]. As an alternative, betaaminosulfonamides have been used which are stable compounds; however, the resulting pseudopeptides show too high a conformation flexibility, as the simple carbon-carbon bond [—HNCHR—CH$_2$SO$_2$—] so introduced in the skeleton of the pseudopeptide induces in the molecule an increase in the freedom degrees thanks to the possibility of rotating around its axis, with ensuing increase in the possible conformations. It is worth stressing that the pharmacological activity largely depends on the conformation state of the molecule that constitutes the active principle.

OBJECTS OF THE INVENTION

An object of this invention is to realize products derived from aminosulfonic acids suitable to be utilized in the synthesis of pseudopeptides provided with bonds stable towards the enzymatic hydrolytic activity. A further object of this invention is to provide products derived from aminosulfonic suitable to be utiized in the synthesis of pseudopeptides, such as to have a potential pharmacological activity.

Another object of this invention is to provide pseudopeptides having a better bioavailability compared with the corresponding peptide compounds, as well as chemical-physical characteristics more favourable for their utilization as enzymatic inhibitors.

Still another object of this invention is to provide a process for the synthesis of derivatives of aminosulfonic acids such as to be of easy industrial realization and application and offering remarkable economic advantages.

A further object of this invention is to realize a process for the use of derivatives of aminosulfonic acids in the synthesis of pseudopeptides comprising at least a sulfonamide bond.

DESCRIPTION OF THE INVENTION

These and still other objects and related advantages which will be more clearly stressed by the following description are achieved by products suitable to be utilized in the synthesis of pseudopeptides, which products, according to this invention, have the following general formula:

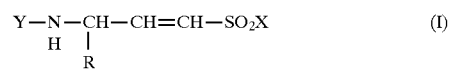

where:
R is chosen among: hydrogen, fragments corresponding to the side chains of the natural aminoacids and in particular the proteinogenic aminoacids, substituted and unsubstituted, linear, branched or cyclic alkyl chains, arylalkyl chains, aryl and heteroaromatic groups;
Y indicates hydrogen, including, in this case, the possible saline forms of the corresponding amine, or any protective group commonly utilized for the protection of amine groups;
X indicates Cl, OH, OCH$_2$CH$_3$, OCH$_3$, ONBu$_4$, NHCH$_2$Ph, provided that:
when Y is chosen among PhCH$_2$CO, (CH$_3$)$_3$COCO, and X is chosen among OCH$_2$CH$_3$, ONBu$_4$
or
when Y is chosen as PhOCH$_2$CO and X is chosen as OCH$_2$CH$_3$
or
when Y is a saline form of the corresponding amine and X is chosen as OH,
R is different from CH$_3$.

More particularly, always according to this invention, said R is chosen among the side chains comprised in proteinogenic aminoacids, said Y is equal to the (CH$_3$)$_3$C—OCO— protective group, said X is equal to OR$_1$, where R$_1$ is chosen among —CH$_3$ and CH$_2$CH$_3$, according to the following formula:

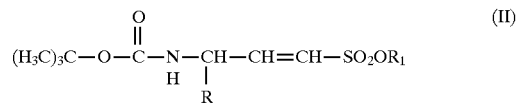

provided that:
when R$_1$ is CH$_2$CH$_3$, R is different from CH$_3$.

Alpha-beta unsaturated sulfonates, namely ethyl and t-butylammonium sulfonates where the protective group of the amine is $(CH_3)_3COCO$, $PhCH_2CO$ or $PhOCH_2CO$, exclusively obtained from alaninal derivatives described in Bull.Soc.Chim.Fr (1990) 127,835–842, (Carretero et al.) as intermediates in the synthesis of alpha-beta epoxysulfonates, were tested as potential inhibitors of bacterial D,D-peptidases.

As has been seen, derivatives according to the present invention having the general formula (I), where R is chosen among: hydrogen, fragments corresponding to the side chains of the natural aminoacids and in particular the proteinogenic aminoacids, substituted and unsubstituted, linear, branched or cyclic alkyl chains, arylalkyl chains, aryl and heteroaromatic groups, Y indicates hydrogen, including, in this case, the possible saline forms of the corresponding amine, or any protective group commonly utilized for the protection of amine groups, X indicates Cl, OH, $OCH_2CH_3$, $OCH_3$, $ONBu_4$, $NHCH_2Ph$, or derivatives of gamma-amino-alpha,beta-unsaturated sulfonic acids, are utilized as syntones in the synthesis of pseudopetides characterized by the presence of at least a sulfonamide bond conjugated to a double bond, for instance according to the following formula:

$$Y-\underset{H}{N}-\underset{R}{CH}-CH=CH-SO_2-\underset{H}{N}-\underset{R_2}{CH}-CH=CH=SO_2X \quad (XIII)$$

where $R_2$ is chosen among hydrogen, fragments corresponding to the side chains of natural aminoacids and in particular proteinogenic aminoacids, substituted or unsubstituted, linear, branched or cyclic alkyl chains, arylalkyl chains, aryl and heteroaromatic groups, and may be equal to R.

In particular, when Y is equal to the protective group $(CH_3)_3C-OCO-$, the formula is the following:

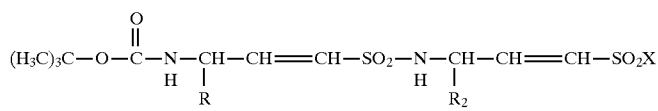

The pseudopeptide compounds obtained by utilizing said derivatives (I) prove to be, always according to this invention, less sensitive to the hydrolytic activity of the enzymes compared with the corresponding peptides, being characterized by the presence of at least a sulfonamide type bond, which, unlike the amide bond, is not subject to hydrolysis by the proteolitic enzymes, being on the contrary a potential inhibitor of the same. As a consequence, the so obtained sulfonamide pseudopeptide is stabler than the corresponding peptide, and thanks to this stability it can reach more easily the target where it may exercise a possible pharmacological activity. Said greater stability to enzymatic hydrolysis can allow, in case of a therapeutical utilization of said sulfonamide pseudopeptide, the administration of a low dosage, with obvious ensuing advantages of general tolerability.

The presence of the double bond in alpha-beta position according to this invention allows to obtain pseudopetides of the sulfonamide type having a greatly increased structural rigidity compared with the analogous pseudopeptides comprising beta-amino,alpha-sulfonic units which lend the derived pseudopeptides, as said, too high a conformation flexibility. The structural rigidity, characteristic of the sulfonamide pseudopeptides obtained by utilizing said derivatives of gamma-amino-alpha,beta-unsaturated sulfonic acids according to this invention, leads to a reduction in the possible conformation states assumed by the molecule; besides, it has been seen that said structural rigidity lends sulfonamide pseudopeptides some characteristics similar to those of the corresponding peptides, which are ascribable, for instance, to the possibility of formation of hydrogen intramolecular bonds, i.e. bonds between the various parts that constitute the molecule. For instance, always according to this invention, the derivative of the formula (I), where:

X is chosen equal to Cl

Y is chosen equal to $(CH_3)_3C-OCO-$

R is chosen equal to Me, is utilized for the preparation of the compound (IV) having the following formula:

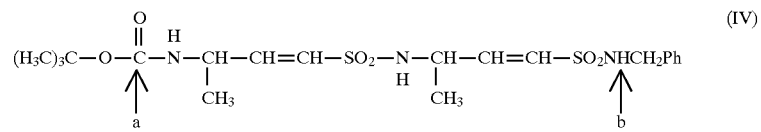

As seen, the compound (IV) in a solution of a suitable solvent, is characterized by the formation of a hydrogen bond between the carbonyl group indicated by "a" and the —NH— group indicated by "b" in the formula; the formation of a hydrogen bond of the aforementioned type obliges the above compound (IV) to assume a space arrangement corresponding to a 14-atom cycle, with relevant conformation constraints which translate into a marked conformation rigidity. As is known, the characteristic conformations of the traditional peptide compounds are partly affected by the possibility of formation of hydrogen intramolecular bonds; such hydrogen bonds limit the possible freedom degrees of the molecule, causing a marked reduction in the possible conformations.

The utilization of derivatives of gamma-amino-alpha,beta-unsaturated sulfonic acids according to this invention to obtain corresponding sulfonamide pseudopeptides, allows also to obtain potential drugs characterized by a satisfactory bioavailability and which are, as a consequence, easily administrable.

Always according to this invention, said derivatives of gamma-amino-alpha,beta-unsaturated sulfonic acids may also be functionalized to the double bond, according to known methods, for instance one can obtain an epoxy group in alpha-beta position, or a cyclopropane group, suitable in any case to lend the molecule rigidity. Said functionalization of the double bond may be performed either on the derivative of the gamma-amino-alpha,beta-unsaturated sulfonic acid of the general formula (I) and utilizing then said so functionalized derivative in the synthesis of said sulfonamide pseudopeptides, or directly on the pseudopeptides characterized by the presence of at least a sulfonamide bond and obtained according to this invention.

According to this invention, the process for the synthesis of said derivatives of gamma-amino-alpha,beta-unsaturated sulfonic acids of the general formula (I), consists in converting, according to known methods, the natural aminoacids into alpha-aminoaldehydes which are in their turn converted into said derivatives (I) through Wittig-Horner's reaction. Always according to this invention, said derivatives of gamma-amino-alpha,beta-unsaturated sulfonic acids (I) may be advantageously obtained starting from proteinogenic aminoacids either in (L) form or in (D) form; said proteinogenic amino acids have a high accessibiity and are sold, for the greatest part, to low prices, which causes the preparation of said derivatives (I) to be easy and economical, even on the industrial plane. Always according to this invention, said pseudopeptides characterized by the presence of at least a sulfonamide bond such as, for instance, that of formula (III), are achieved by a process comprising, for instance, the conversion of the gamma-amino-alpha,beta-unsaturated sulfonic ester (II), where said R is chosen among the side chains comprised in proteinogenic aminoacids, said Y is equal to the $(CH_3)_3COCO$— protective group, said X is equal to $OR_1$, where $R_1$ is chosen among —$CH_3$ and —$CH_2CH_3$, into a sulfonated salt, which is then submitted to activation and coupled to a compound having a suitable reactive group, such as, for instance, the same group of formula (II) wherein the amine group has been priorly released. The so obtained product (III) may be submitted to further treatments, which provide for instance for the possibility of an alternated release and activation of either the sulfonic group or the amine group and the ensuing coupling of said product (III) with the same compound (II) previously released in a suitable position, realizing in this way a method of synthesis of sulfonamide pseudopeptides according to this invention of the iterative type, based on protection, release and coupling methods.

Always according to this invention, said derivative (II) may be submitted to release alternatively at the sulfonic ester or the amine group and iteratively coupled with natural aminoacids.

Besides, this process has proved to be especially suitable, inasmuch is keeps substantially unaltered the stereochemical characteristic of the starting products, allowing in this way to perform the already described various protection, release and activation steps in a stereoconservative way. The sulfonamide pseudopeptides obtained through this process and according to this invention, are optically pure, considering the instrumental limits of the experiments carried out to determine such purity.

EXAMPLE 1

According to this invention, the synthesis of the compound having the following formula:

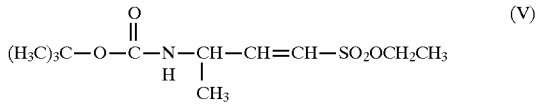

is carried out as described above, and is expounded by way of non limitative example of this invention.

a) Preparation of N-BOC-Alaninol.

A solution constituted by 1 g (0,0112 moles) of (S) alaninol dissolved in 22 ml of methylene chloride was treated with 2,45 g (0,0112 moles) of $(BOC)_2O$ at a temperature of 0° C. under stirring room temperature, the solvent was evaporated and the residue was dissolved in 20 ml of diethyl ether. The ether phase so obtained was washed with a solution of $H_3PO_4$ 0,5M and then treated with brine, then with a solution of $NaHCO_3$ 1,0M, then again with brine. The organic phase was anhydrified on sodium sulfate, the solvent was low pressure evaporated, and 1,95 g (99% yield) of (S) N-BOC-alaninol were obtained.

$^1$H-NMR (200 MHz, ppm, $CDCl_3$): 1,15 (3H,d,J=6,7 Hz); 1,46 (9H,s,); 2,1 (1H,broad); 3,5 (1H,m); 3,65 (2H,m); 4,66 (1H,broad).

b) Preparation of N-BOC-Alaninal.

A solution constituted by 1,9 g (1,3 ml, 15 mmoles) of oxalylchloride in 12 ml of methylene chloride was treated under nitrogen and at a temperature of −63° C. with a solution constituted by 1,58 g of dymethylsulfoxide (1,435 ml, 20 mmoles) in 6,1 ml of methylene chloride.

To the resulting solution was then added within a time period of 30 minutes a solution constituted by 1,75 g of (S) N-BOC-alaninol (10 mmoles) dissolved in 71,4 ml of methylene chloride. After 10 minutes, a solution of 4,07 g of triethylamine (5,61 ml, 40 moles) in 12,2 ml of methylene chloride was added to the reaction mix; said addition was made in 20 minutes, and a clouding of the reaction mix was observed. The TLC analysis eluent hexane : ethyl acetate 1:1 [v/v]) has shown that after 10 minutes at a temperature of −63° C. the reaction was completed. The reaction was then interrupted by a slow addition of 8 ml of water, keeping always the temperature at −63° C. and the reaction mix under vigorous stirring.

The mix was then quickly poured in 120 ml of n-hexane and washed with 50 ml of a $KHSO_4$ solution obtained by diluting 10 ml of a $KHSO_4$ saturated solution with 40 ml of water. The aqueous phase was extracted with ethyl ether. The so obtained organic phases were combined, washed with a saturated solution of $NaHCO_3$ (2×45 m), with water (3×45 ml) and brine (2×45 ml). The so obtained organic phase was anhydrified with sodium sulfate, the solvent was low pressure evaporated, and 1,6 g of (S) N-BOC-Alaninal (92% yield) were obtained.

$^1$H-NMR (200 MHz, ppm, $CDCl_3$): 1,35 (3H,d, J=6,5 Hz); 1,46 (9H,s); 4,25 (1H,m); 5,1 (1H,broad); 9,57 (1H,s).

c) Preparation of apha,beta-unsaturated ethyl sulfonate (V).

A solution of 5,0 g of ethyl-diethylfosforyl-methansufonate $(EtO)_2PO$—$CH_2SO_3Et$ (19,2 mmoles) (prepared as described in CARRETERO J. C. et al. Tetrahedron 43,5125 [1987]) in 72,0 ml of THF was treated under nitrogen at a temperature of −78° C. with 13,2 ml (21,1 mmoles) of a solution of 1,6M of n-BuLi in n-haxane. The mix was kept for 20 minutes under stirring at a temperature of −78° C., then 3,3 g (19,2 mmoles) of (S) N-BOC-Alaninal obtained as descrived under b) dissolved in 5,0 ml of THF were added. After 30 minutes the reaction was interrupted by treating the mix with phosphate buffer, pH 7, and the aqueous phase was extracted with ethyl ether. The organic phases extracted were combined and anhydrified on sodium sulfate and the solvent was low pressure evaporated. The so obtained raw mix was purified by means of flash chromatography, utilizing n-hexane:ethyl acetate 7:3 (v/v) as eluent mix, and 4,18 g of sulfonate (V) (78% yield) were obtained.

$^1$H-NMR (200 MHz, ppm, $CDCl_3$): 1,33 (3H,d, J=6,9 Hz); 1,39 (3H,t, J=7,2 Hz); 1,46 (9H,s); 4,18 (2H,q, J=7,2 Hz); 4,44 (1H,m); 4,6 (1H,broad); 6,30 (1H,dd, J=15,10 Hz, J=1,61 Hz); 6,83 (1H,dd J=15,10 Hz, J=4,96 Hz), $^{13}$C-NMR (200 MHz, ppm, $CDCl_3$): 14,65 ($CH_3$); 19,58 ($CH_3$); 28,13 ($[CH_3]_3$); 47,14 (CHN); 66,85 ($CH_2$); 123,86 (CH=); 149,61 (CH=).

m.p.=69°–71° C.

$[\alpha]_D$=−18.060 (c=0.98, $CHCl_3$)

EXAMPLE 2

Always according to this invention, the compound having the following formula:

$$(H_3C)_3C-O-\underset{\underset{H}{|}}{\overset{\overset{O}{\|}}{C}}-N-CH-CH=CH-SO_2OCH_2CH_3 \quad (VI)$$
$$\underset{H_3C\diagup \diagdown CH_3}{CH}$$

is synthesized as described hereunder, always by way of non limitative example of this invention.

a) Preparation of N-BOC-Valinol.

Starting from (S) Valinol and following the procedure described for Example 1, point a), (S) N-BOC-Valinol was obtained in 97% yields.

$^1$H-NMR (200 MHz, ppm, CDCl$_3$): 0,93 (3H,d, J=6,7 Hz); 0,96 (3H,d, J=6,7 Hz); 1,46 (9H,s); 1,85 (1H,m); 2,35 (1H,broad); 3,45 (1H,m); 3,66 (2H,m); 4,65 (1H,broad).

b) Preparation of N-BOC-Valinal.

Starting from (S) N-BOC-Valinol and following the procedure described in Example 1, point b), (S) N-BOC-Valinal was obtained in 90% yields.

$^1$H-NMR (200 MHz, ppm, CDCl$_3$): 0,95 (3H, d, J=6,5 Hz); 1,05 (3H,d, J=6,5 Hz); 1,45 (9H,s); 2,30 (1H,m); 4,25 (1H,m); 5,22 (1H,broad); 9,65 (1H,s).

c) Preparation of alpha,beta-unsaturated ethyl sulfonate (VI).

Starting from (S) N-BOC-Valinal and following the procedure described in Example 1, point c), the sulfonate of the formula (VI) was obtained in 77% yields.

$^1$H-NMR (200 MHz, ppm, CDCl$_3$): 0,96 (3H,d, J=6,4 Hz); 0,98 (3H,d, J=6,4 Hz); 1,39 (3H,t, J=7,5 Hz); 1,47 (9H,s); 1,92 (1H,m, J=6,4 Hz); 4,27 (2H,q, J=7,5 Hz); 4,15 (1H,m); 4.6 (1H,broad); 6,32 (1H,dd, J=14,90 Hz, J=1,90 Hz); 6,82 (1H,dd, J=14,90 Hz, J=4,80 Hz).

$^{13}$C-NMR (200 MHz, ppm, CDCl$_3$): 14,69 (CH$_3$); 17,95 (2×CH$_3$); 18,74 (CH$_3$); 28,14 ([CH$_3$]$_3$); 31,78 (CH[Me$_2$]); 56,38 (CHN); 66,81 (CH$_2$); 125,16 (CH=); 147,63 (CH=). m.p.=53°–55° C. [α]$_D$=+3.15° (c=1.0, CHCl$_3$)

EXAMPLE 3

Always according to this invention, the compound having the following formula:

$$(H_3C)_3C-O-\underset{\underset{H}{|}}{\overset{\overset{O}{\|}}{C}}-N-CH-CH=CH-SO_2OCH_3 \quad (VII)$$
$$\underset{CH_3}{|}$$

was prepared as described hereunder, always by way of non limitative example of this invention.

The procedure described in Example 1, points a), b) and c) was followed starting from (S) alaninol, but methyl-diethyl-fosforyl-methanephosphonate (EtO)$_2$PO—CH$_2$SO$_3$Me was utiized instead of ethyl-diethylfosforyl-methansulfonate (EtO)$_2$PO—CH$_2$SO$_3$Et.

The raw mix was purified by flash chromatography, utilizing n-hexane:ethyl acetate 75:25 (v/v) as eluent mix and crystallized (n-hexane/ethyl acetate 7/3); alpha-beta-unsaturated methyl sulfonate (VII) was obtained with a 75% yield.

m.p.=89°–91° C.

[alpha]$_D$=−22,3° C. (c 1,0, CHCl$_3$)

$^1$H-NMR (200 MHz, ppm, CDCl$_3$): 1,33 (3H,d, J=7.0 Hz); 1,45 (9H,s); 3,82 (3H,s); 4,45 (1H,m); 4,61 (1H,d, J=4,40 Hz); 6,27 (1H,dd, J=15,10 Hz, J=1,60 Hz); 6,86 (1H,dd, J=15,10Hz, J=4,97 Hz).

$^{13}$C-NMR (200 MHz, ppm, CDCl$_3$): 19,61 (CH$_3$); 28,15 ([CH$_3$]$_3$; 46,75 (CHN); 56,16 (OCH$_3$); 122,71 (CH=); 150,66 (CH=).

EXAMPLE 6

(S) N-BOC-Prolinol. Following the above procedure the desired alcohol is obtained in 98% yield.

$^1$H-NMR (d, CDCl$_3$): 1.49 (9H, s, [CH$_3$]$_3$C); 1.7–1.9 (2H, m, NCHCH$_2$CH$_2$); 1.9–2.1 (2H, m, NCHCH$_2$); 3.2–3.55 (2H, m, NCHCH$_2$CH$_2$CH$_2$); 3.6 (2H, m, CH$_2$OH); 3.95 (1H, m, NCH)); 4.78 (1H, broad, OH).

(S) N-BOC-Prolinal. Following the above procedure, (S) N-BOC-Prolinal is obtained in 96% yield.

$^1$H-NMR (d, CDCl$_3$): 1.45 (9H, s, [CH$_3$]$_3$C); 1.78–2.08 (4H, m, NCHCH$_2$CH$_2$); 3.43 (2H, m, CH$_2$NCH); 4.1 (1H, broad, NCH); 9.43 (1H, s, CHO).

Following the above described procedure, a crude mixture was obtained which was purified by flash chromatography (n-hexane/AcOEt=6/4) to give the desired sulfonate (XX) in 60% yield.

[α]$_D$=6.56° (c=1.01, CHCl$_3$).

$^1$H-NMR (d, CDCl$_3$): 1.44 (9H, s, [CH$_3$]$_3$C); 1.76–1.95 (3H, m, NCHCHHCH$_2$); 2.2 (1H, m, NCHCHH); 3.43 (2H, m, NCHCH$_2$CH$_2$CH$_2$); 3.81 (3H, s, OCH$_3$); 4.5 (1H, m, NC H); 6.186 (1H, dd, CH=CHSO$_3$, J=15.07 Hz, J=0.93Hz); 6.8 (1H, dd, CH=CHSO$_3$, J=15.06 Hz, J=5.67 Hz).

$^{13}$C-NMR (d, CDCl$_3$): 20.905 (CH$_2$); 28.222 ([CH$_3$]$_3$); 31.430 (CH$_2$); 46.309 (CH$_2$); 55.052 (CH); 57.083 (OCH$_3$); 123.127 (CH=); 149.312 (CH=).

$$\underset{\underset{BOC}{|}}{\underset{N}{\diagup\diagdown}}CH=CH-SO_2-OCH_3 \quad (XX)$$

Likewise, sulfonate (XXI) has been prepared, which was obtained as a crude mixture and was purified by flash chromatography (n-hexane/AcOEt=90/10) to give the desired product in 46% yield.

$$BOC-NH-\underset{\underset{CH_2OSitBuPh_2}{|}}{CH}-CH=CH-SO_2-OCH_2CH_3 \quad (XXI)$$

$^1$H-NMR (d, CDCl$_3$): 1.08 (9H, s, [CH$_3$]$_3$CSi); 1.36 (3H, t, OCH$_2$CH$_3$, J=7.1 Hz); 1.47 (9H, s, [CH$_3$]$_3$CO); 3.79 (2H, m, OCH$_2$CH); 4.17 (2H, q, OCH$_2$CH$_3$, J=7.1 Hz); 4.45 (1H, m, CHN); 4.96 (1H, d, NH, J=8.3 Hz); 6.39 (1H, dd, CH=C HSO$_3$, J=1.6 Hz, J=15.1 Hz); 6.9 (1H, dd, CH=CHSO$_3$, J=4.7 Hz, J=15.1 Hz); 7.3–7.7 (10H, m, 2 × PhSi).

$^{13}$C-NMR (d, DEPT, CDCl$_3$): 14.728 (OCH$_2$CH$_3$); 26.751 ([CH$_3$]$_3$CSi); 28.174 ([CH$_3$]$_3$CO); 52.621 (CH); 64.707 (CHCH$_2$O); 66.835 (OCH$_2$CH$_3$); 125.754 (CH=CHS); 127.886 (CH=); 130.024 (CH=); 135.455 (CH=); 146.623 (CH=CHS).

Always following the described procedure, sulfonate (XXII)has been obtained as a crude mixture and was purified by flash chromatography (n-hexane/AcOEt=65/35) to give the desired product in 56% yield.

$$BOC-NH-\underset{\underset{CH_2CH_2CONHCPh_3}{|}}{CH}-CH=CH-SO_2-OCH_2CH_3 \quad (XXII)$$

$^1$H-NMR (d, CDCl$_3$): 1.37 (3H, t, CH$_3$CH$_2$O, J=7.1 Hz); 1.44 (9H, s, [CH$_3$]$_3$C); 1.82–1.94 (2H, m, CH$_2$CH$_2$CO); 2.41 (2H, t, CH$_2$CH$_2$CO, J=6.69 Hz); 4.155 (2H, q, OCH$_2$CH$_3$, J=7.1 Hz); 4.31 (1H, m, NHCH); 5.13 (1H, d, NHCH, J=5.6 Hz); 6.25 (1H, d, CH=CHSO$_3$, J=15.19 Hz); 6.75 (2H, dd,

C*H*=CHSO$_3$+N*H*CPh$_3$, J=5.25 Hz, J=15.2 Hz); 7.18–7.32 (15H, m, Ar*H*).

$^{13}$C-NMR (d, DEPT, CDCl$_3$): 14.702 (CH$_3$); 28.195 [(CH$_3$)$_3$]; 29.582 (CH$_2$); 33.072 (CH$_2$); 56.762 (CHN); 66.986 (OCH$_2$); 124.866 (CH=); 126.992 (CH=); 127.800 (CH=); 128.534 (CH=); 148.025(CH=).

EXAMPLE 4

The above described process, which allows to obtain pseudopeptides characterized by the presence of at least a sulfonamide bond according to this invention, may be schematized as follows when, for instance, the product (V) is utilized as a starting material:

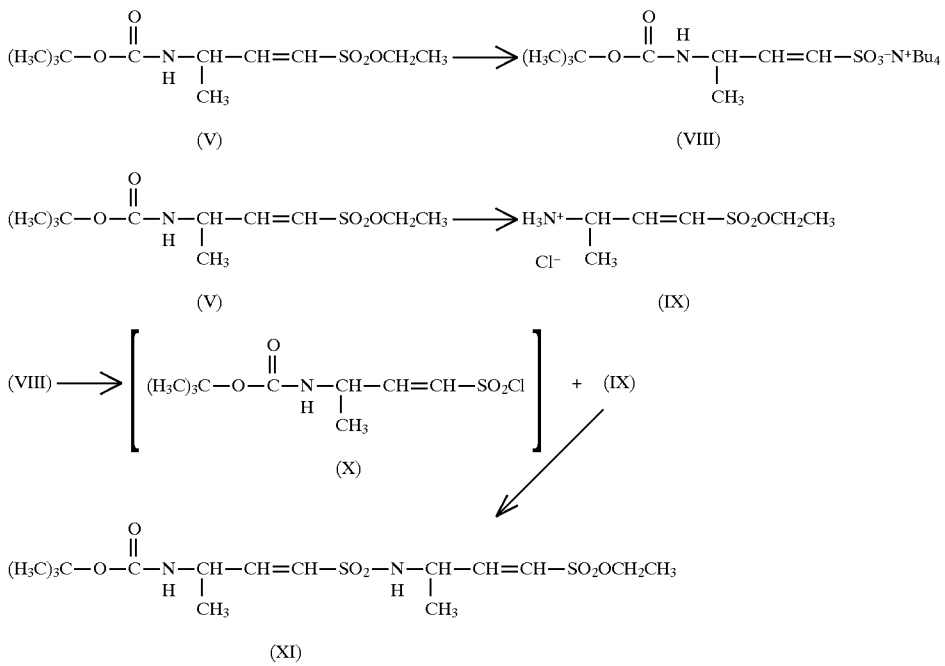

SCHEME 1 and is described in details in the examples given hereunder.

a) Preparation of sulfonate salt (VIII).

A solution of 1,0 g (3,6 mmoles) of alpha,beta-unsaturated ethyl sulfonate (V) in 20 ml of acetone was treated, in nitrogen atmosphere and under stirring, with 1, 33 g (3,6 mmoles) of n-Bu$_4$NI recrystallized by a 95/5 ethyl acetate/methanol mix.

A reflux of the reaction mix was allowed for 16 hours, checking by means of TLC the progressive disappearance of the starting product, utilizing n-hexane:ethyl acetate 6:4 (v/v) as eluent system. After low pressure evaporation of the solvent, 1,774 g of sulfonate salt (VIII) (100% yield) were obtained.

$^1$H-NMR (200 MHz, ppm, CDCl$_3$): 1,0 (12H,t, J=7,6 Hz); 1,20 (3H,d, J=6,8 Hz); 1,40 (9H,s); 1,4–1,8 (16H,m); 3,3 (8H,m); 4,30 (1H,m); 4,45 (1H,broad); 6.42 (2H,m).

b) Preparation of amine hydrochloride (IX).

250 mg (0,89 mmoles) of apha,beta-unsaturated ethyl sulfonate (V) were treated with 5 m of a HCl M solution in methyl alcohol, in nitrogen atmosphere and at a temperature of °C. The reaction mix was kept under stirring at °C. for 5 hours, checking by means of TLC the progressive disappearance of the starting product, utilizing a n-hexane:ethyl acetate 6:4 (v/v) as eluent system. The solvent was then low pressure evaporated and the resulting product was placed under vacuum (0,1 mmHg). 192 mg (100% yield) of hydrochloride salt were obtained, which was utilized in the subsequent reactions without further purifications.

c) Preparation of sulfonamide pseudopeptides (XI).

180 mg (0,107 ml, 1,33 moles) of suforyl chloride were added to a solution of 320 mg of triphenylphosphine Ph$_3$P (1,224 mmoles) in 1,5 ml of methylene chloride at 0°, under nitrogen and in the presence of 3 A° molecular sieves. A solution of 302 mg (0,611 mmoles) of sulfonate salt (VIII) in 2,0 ml of methylene chloride was then added under stirring, at room temperature and under nitrogen.

The reaction mix was kept under stirring at room temperature for 150 minutes, then the solvent was low pressure removed and the raw product putified by means of flash chromatography, utilizing n-hexane:ethyl acetate 6:4 (v/v) as eluent mix. 142 mg of sulfonyl chloride (X) (85% yield ) were obtained.

$^1$H-NMR (ppm, 200 MHz, CDCl$_3$): 1,32 (3H,d, J=7,1 Hz); 1,42 (9H,s); 4,5 (1H,broad); 5,0 (1H,broad); 6,80 (1H,dd, J=14,80 Hz, J=1,09 Hz); 6,97 (1H,dd, J=14,80 Hz, J=4,40 Hz).

$^{13}$C-NMR (ppm, 200 MHz, CDCl$_3$): 19,364 (CH$_3$); 28,144 ([CH$_3$]$_3$); 46,488 (CHN); 132,678 (CH=); 150,425 (CH=); 154,648 (C=O).

142 mg (0,525 mmoles) of sulfonyl chloride (X) obtained as described above were dissolved in 4,0 ml of methylene chloride and then a solution was added all at once constituted by 74,6 mg (0,35 mmoles) of (IX) in 2,0 ml of methylene chloride, comprising 0,052 ml (0,35 mmoles) of DBU and 8,4 mg (0,070 mmoles) of 4-dimethylaminopyridine (DMAP).

After the addition, 0,078 ml (0,525 mmoles) of DBU in 1,0 ml of methylene chloride were furtherly added, slowly and during a period of three hours. A reflux of the mix was allowed for 5 hours, then the mix was diluted with methylene chloride and treated with 2,0 ml of pH 7 phosphate buffer. The aqueous phase was extracted with methylene chloride, the organic extracts were combined, anhydrified on sodium sulfate and evaporated. A raw product was obtained which was purified by means of flash chromatography, utilizing a n-hexane:ethyl acetate mix 1:1 (v/v) as eluent, obtaining (XI) with 50% yields.

$^1$H-NMR (200 MHz, ppm, CDCl$_3$): 1,32 (3H,d, J=7,1 Hz); 1,39 (3H,d, J=7,0 Hz); 1,41 (3H,t, J=7,0 Hz); 1,46 (9H,s); 4,15 (1H,m); 4,22 (2H,q, J=7,0 Hz); 4,36 (1H,m); 4,75 (2H,m); 6,30 (1H,dd, J=15,0 Hz, J=1,2 Hz); 6,47 (1H,dd, J=15,1, J=1,3 Hz); 6,68 (1H,dd, J=15,0 Hz, J=5,4 Hz); 6,82 (1H,dd, J=15,1 J=5,2 Hz).

$^{13}$C-NMR (200 MHz, ppm, CDCl$_3$): 15,51 (CH$_3$); 20,30 (CH$_3$); 21,51 (CH$_3$); 28,91 ([CH$_3$]$_3$); 47,4 (CH); 50,23 (CH); 50,23 (CH); 67,91 (OCH$_2$); 126,26 (CH=); 128,61 (CH=); 147,47 (CH=); 148,73 (CH=); 157 (O—C=O).

EXAMPLE 5

Always according to this invention, the compound (XII) having the following formula:

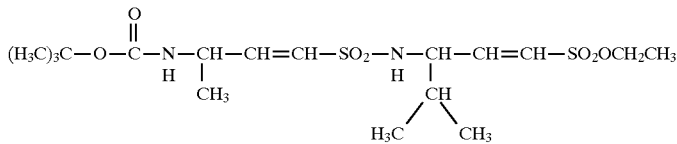

(XII)

was prepared according to the methods already described in Examples 4, 5 and 6, starting from the compound (V) and the compound (VI); said compound (XII) was obtained in raw form and purified and characterized as described hereunder.

The raw product (XII) was purified by means of flash chromatography, utilizing a n-hexane:ethyl acetate mix 6:4 (v/v).

$^1$H-NMR (200 MHz, ppm, CDCl$_3$): 0,98 (3H,d, J=6,8 Hz); 0,99 (3H, d, J=6,8 Hz); 1,30 (3H,d, J=7,1 Hz); 1,41 (3H,t, J=7,1 Hz); 1,45 (9H,s); 1,94 (1H,m); 3,86 (1H,m); 4,23 (2H,q, J=7,1 Hz); 4,39 (1H,m); 4,75 (2H,m); 6,29 (1H,dd, J=15,1 Hz, J=1,4Hz); 6,47 (1H,dd, J=15,2 Hz, J=1,2 Hz); 6,68 (1H,dd J=15,1 Hz, J=5,3 Hz); 6,80 (1H,dd, J=15,2 Hz, J=6,0 Hz).

$^{13}$C-NMR (200 MHz, ppm, CDCl$_3$): 14,80 (CH$_3$); 18,04 (CH$_3$); 18,59 (CH$_3$); 27,97 (CH$_3$); 28,21 ([CH$_3$]$_3$); 32,28 (CH); 46,51 (CHN); 56,19 (CHN); 67,21 (OCH$_2$); 126,91 (CH=); 127,89 (CH=); 146,22 (CH=); 146,67 (CH=).

EXAMPLE 7

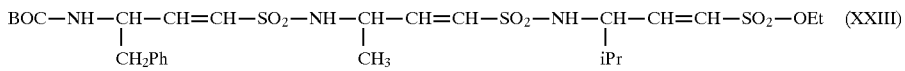

To the product (I) where: Y=BOC, R=CH$_2$Ph, X=Cl (181.5 mg, 0.525 mmol) in CH$_2$Cl$_2$ (4 ml), a solution of (XII) as amine hydrochloride (131.9 mg, 0.35 mmol) in CH$_2$C$_2$ (1 ml) was added, containing DBU (0.052 ml, 0.35 mmol) and DMAP (8.4 mg, 0.070 mmol). More DBU (0.078 ml, 0.525 mmol) in CH$_2$Cl$_2$ (1 ml) and more sulfonyl chloride (60.5 mg, 0.175 mmol) were then added. After 5 hours, the reaction mixture was diluted with CH$_2$Cl$_2$ and phosphate buffer was added (2 ml). The aqueous phase was extracted with CH$_2$Cl$_2$ and the collected and dried organic extracts were evaporated, to give a crude mixture which was purified by flash chromatography (n-hexane/AcOEt=55/45) to give product (XXIII) in 60% yield.

$^1$H-NMR (500 MHz, d, CDCl$_3$): 0.95 (3H, d, C$\underline{H}_3$CHC, J=7.5 Hz); 0.97 (3H, d, C$\underline{H}_3$CHC, J=7.0 Hz); 1.31 (3H, d, C$\underline{H}_3$CHN, J=6.5 Hz); 1.38 (9H, s, [C$\underline{H}_3$]$_3$C); 1.40 (3H, t, C$\underline{H}_3$CH$_2$OSO$_2$, J=7.0 Hz); 1.88 (1H, m, Me$_2$C$\underline{H}$C); 2.82 (1H, dd, C$\underline{H}$HPh, J=14.0 Hz, J=7.0 Hz); 3.01 (1H, broad, d, CH$\underline{H}$Ph, J=14.0 Hz); 3.90 (1H, q, Me$_2$C$\underline{H}$CHN, J=7.5 Hz); 4.13 (1H, m, CH$_3$ C$\underline{H}$N); 4.23 (2H, m, CH$_3$C$\underline{H}_2$OSO$_2$); 4.60 (2H, m, PhCH$_2$C$\underline{H}$N+MeCHN$\underline{H}$); 4.65 (1H, m, PhCH$_2$CHN$\underline{H}$); 5.76 (1H, d, Me$_2$CHCHN$\underline{H}$, J=8.5 Hz); 6.216 (1H, d, Bn—CHCH=C$\underline{H}$, J=15.0 Hz); 6.316 (1H, d, MeCHCH=C$\underline{H}$, J=15.4 Hz); 6.398 (1H, d, i—PrCHCH=C$\underline{H}$, J=15.3 Hz); 6.477 (1H, dd, MeCHC$\underline{H}$=CH, J=15.4 Hz, J=5.0 Hz), 6.748 (1H, dd, i—PrCHC$\underline{H}$=CH, J=15.3 Hz, J=7.5 Hz); 6.810 (1H, dd, BnCHC$\underline{H}$=CH, J=15.0 Hz, J=4.0 Hz); 7.16 (2H, d, Ar$\underline{H}$, J=7.0 Hz); 7.24 (1H, t, Ar$\underline{H}$, J=6.0 Hz); 7.30 (2H, t, Ar $\underline{H}$, J=7.5 Hz).

$^{13}$C-NMR (d, CDCl$_3$): 14.89 (CH$_3$); 18.19 (2×CH$_3$); 18.73 (CH$_3$); 28.19 ([CH$_3$]$_3$); 32.48 (CH); 39.79 (C$\underline{H}_2$Ph); 49.23 (CHN); 52.11 (CHN); 59.89 (CHN); 67.09 (OC$\underline{H}_2$); 126.67 (CH=); 127.01 (Ar); 128.65 (Ar); 128.72 (CH=); 129.20 (Ar); 130.05 (Ar); 143.00 (CH=); 144.87 (CH=); 146.08 (CH=); 155.32 (C=O).

Product (XXIV), having the following formula, was prepared always according to the present invention:

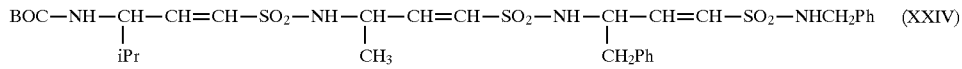

in 32% yield.

$^1$H-NMR (d, CDCl$_3$): 0.95 (3H, d, C$\underline{H}_3$CH, J=6.8 Hz); 0.96 (3H, d, C$\underline{H}_3$CH, J=6.7 Hz); 1.24 (3H, d, C$\underline{H}_3$CH, J=6.99 Hz); 1.40 (9H, s [C$\underline{H}_3$]$_3$C); 1.85 (1H, m, Me$_2$C$\underline{H}$); 2.82 (1H, dd, CHC$\underline{H}$HPh, J=6.93 Hz, J=13.5 Hz); 3.0 (1H, dd, CHCH$\underline{H}$Ph, J=4.2 Hz, J=13.5 Hz); 3.8–4.0 (2H, m, iPrC$\underline{H}$N+MeC$\underline{H}$N); 4.16 (2H, d, NC$\underline{H}_2$Ph, J=6.1 Hz); 4.5–4.7 (2H, m, BnC$\underline{H}$N+CHN$\underline{H}$); 4.85 (1H, d, N$\underline{H}$, J=8.6 Hz); 5.4 (1H, t, N$\underline{H}$CH$_2$Ph, J=6.1 Hz); 5.65 (1H, d, N$\underline{H}$, J=9.04 Hz); 6.2–7.0 (6H, m, 3×C$\underline{H}$=CH); 7.1–7.4 (10H, m, Ar$\underline{H}$).

EXAMPLE 8

Likewise, according to the preceding examples, the following products were prepared:

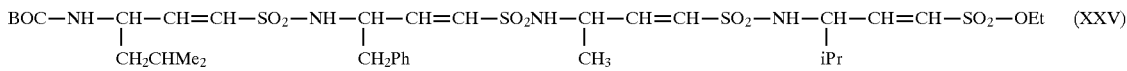

BOC—NH—CH—CH=CH—SO$_2$—NH—CH—CH=CH—SO$_2$NH—CH—CH=CH—SO$_2$—NH—CH—CH=CH—SO$_2$—OEt (XXV)
    |                                  |                              |                          |
    CH$_2$CHMe$_2$                      CH$_2$Ph                        CH$_3$                     iPr obtained in 60% yield.

$^1$H-NMR (500 MHz, d, CDCl$_3$): 0.92 (6H, t, (CH$_3$)$_2$CHCH$_2$, J=6.9 Hz); 0.96 (3H, d, CH$_3$CHC, J=6.5 Hz); 0.97 (3H, d, CH$_3$CHC, J=6.8 Hz); 1.32 (2H, m, CHCH$_2$C); 1.35 (3H; d, CH$_3$CHN, J=6.9 Hz); 1.39 (3H, t, CH$_3$CH$_2$OSO$_2$, J=7.0 Hz); 1.43 (9H, s, [CH$_3$]$_3$C); 1.65 (1H, m, Me$_2$CHCH$_2$); 1.90 (1H, m, Me$_2$CHC); 2.77 (1H, dd, CHHPh, J=13.9 Hz, J=8.4 Hz); 3.03 (1H, dd, CHHPh, J=13.9 Hz, J=5.3 Hz); 3.90 (1H, m, Me$_2$CHCHN); 4.15–4.32 (5H, m, CH$_3$CHN+PhCH$_2$CHN+iBUCHN+CH$_3$CH$_2$OSO$_2$, J=7.0 Hz); 4.39 (1H, d, iBUCHNH, J=7.7 Hz); 4.52 (1H, d, PhCH$_2$CHNH, J=5.5 Hz); 4.96 (1H, d, iPrCHNH, J=8.2 Hz); 5.39 (1H, d, MeCHNH, J=7.0 Hz); 5.91 (1H, d, BnCHCH=CH, J=15.0 Hz); 6.35 (1H, d, CH=CH, J=14.6 Hz); 6.42 (1H, d, CH=CH, J=14.0 Hz); 6.44 (1H, d, iPrCHCH=CH, J=14.8 Hz); 6.53 (1H, dd, MeCHCH=CH, J=14.7 Hz, J=5.9 Hz); 6.59 (1H, dd, BnCHCH=CH, J=15.0 Hz, J=5.1 Hz); 6.63 (1H, dd, CHCH=CH, J=15.1 Hz, J=6.4 Hz); 6.74 (1H, dd, iPrCHCH=CH, J=14.8 Hz, J=6.8 Hz); 7.18 (2H, d, ArH); 7.30 (1H, t, ArH); 7.35 (2H, t, ArH).

$^{13}$C-NMR (DEPT, d, CDCl$_3$): 14.85 (CH$_3$); 18.20 (CH$_3$); 18.63 (CH$_3$); 21.21 (CH$_3$); 21.66 (CH$_3$); 22.83 (CH$_3$); 24.58 (CH); 28.24([CH$_3$]$_3$); 32.39 (CH); 40.37 (CH$_2$); 43.14 (CH$_2$); 49.03 (CHN); 49.57 (CHN); 55.21 (CHN); 59.56 (CHN); 67.27 (OCH$_2$); 126.62 (CH=); 127.24 (CH=); 128.31 (CH=); 128.55 (CH=); 128.81 (CH=); 129.71 (CH=); 129.77 (CH=); 130.33 (CH=); 131.90 (CH=); 132.10 (CH=); 143.48 (CH=); 144.26 (CH=); 146.36 (CH=).

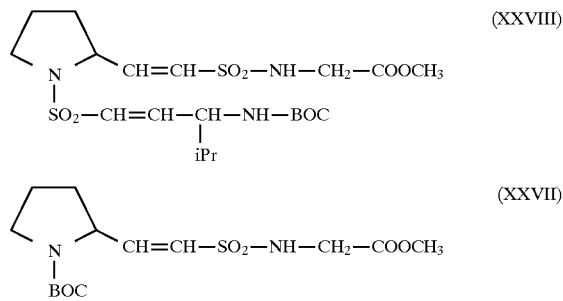

To a solution of (XX) (200 mg, 0.67 mmol) converted into the corresponding sulfonil chloride according to the already described procedures in CH$_2$Cl$_2$ (6.7 ml), under nitrogen, Gly methylester hydrochloride salt (169.8 mg, 1.35 mmol), DBU (205.8 mg, 1.35 mmol, 201.4 μl) and DMAP (16.5 mg, 0.135 mmol) in CH$_2$Cl$_2$ (2 ml) were added. After 30 min, more DBU (0.5 eq, 50.3 μl, 0.34 mmol) was added. After 30 min, 0.5 eq of sulfonil chloride (100 mg, 0.33 mmol) and 0.5 eq of DBU (0.34 mmol, 50.3 μl) were added. After 1 h phosphate buffer (10 ml) was added, the aqueous phase was extracted with CH$_2$Cl$_2$ and the collected organic extracts were dried (Na$_2$SO$_4$) and the solvent evaporated under vacuum. The crude mixture so obtained was purified by flash chromatography (n-pentane/AcOEt=4/6) to give (XXVII) (285 mg, 80% yield).

$^1$H-NMR (d, CDCl$_3$) : 1.44 (9H, s, [CH$_3$]$_3$C); 1.75 (3H, m, NCHCHHCH$_2$); 2.15 (1H, m, NCHCHHCH$_2$); 3.4 (2H, broad, NCHCH$_2$CH$_2$CH$_2$); 3.75 (3H, s, OCH$_3$); 3.8 (2H, d,

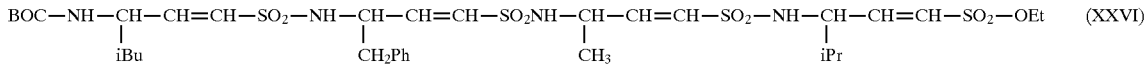

BOC—NH—CH—CH=CH—SO$_2$—NH—CH—CH=CH—SO$_2$NH—CH—CH=CH—SO$_2$—NH—CH—CH=CH—SO$_2$—OEt (XXVI)
    |                                  |                              |                          |
    iBu                                 CH$_2$Ph                        CH$_3$                     iPr obtained in 30% yield.

$^1$H-NMR (d, CDCl$_3$): 0.92 (3H, d, CH$_3$CHCH$_3$, J=6.6 Hz); 0.93 (3H, d, CH$_3$CHCH$_3$, J=6.7 Hz); 1.25–1.35 (5H, m, CH$_3$CH+iPrCH$_2$); 1.45 (9H, s, [CH$_3$]$_3$C); 1.64 (1H, m, Me$_2$CHCH$_2$); 1.83 (1H, m, Me$_2$CH); 2.72 (1H, dd, CHCHHPh, J=9 Hz, J=13.9 Hz); 3.0 (1H, dd, CHCHHPh, J=4.9 Hz, J=13.9 Hz); 3.84 (1H, m, iPrCHN); 4.04 (1H, m, MeCHN); 4.1–4.3 (2H, m, BnCHN+iBuCHN); 4.2 (2H, d, NCH$_2$Ph, J=6.21 Hz); 5.45–5.9 (5H, m, 5×NH); 6.35–6.9 (8H, m, 4×CH=CH); 7.2–7.4 (10H, m, ArH).

$^{13}$C-NMR (DEPT, d, CDCl$_3$): 18.014 (CH$_3$); 18.715 (CH$_3$); 20.944 (CH$_3$); 21.651 (CH$_3$); 22.821 (CH$_3$); 24.582 (CHCH2); 28.225 ([CH3]3C); 32.535 (CH[CH3]2); 40.264 (CH2Ph); 43.077 (CH2CH); 46.925 (NCH2Ph); 49.060 (NCH); 49.559 (NCH); 55.208 (NCH); 59.363 (NCH); 126.815; 127.269; 127.870; 127.975; 128.684; 128.836; 129.705; 129.901; 130.267; 130.656; 142.020 (CH=); 143.490 (CH=); 143.767 (CH=); 146.483 (CH=).

EXAMPLE 9

Always according to the present invention, following the synthetic schemes as reported in the preceding examples, product (XXVIII) was prepared as indicated as follows:

CH$_2$COOCH$_3$, J=4.35 Hz); 4.4 (1H, broad, NCH); 4.95 (1H, t, NHCH$_2$COOMe, J=4.3 Hz); 6.2 (1H, dd, CH=CHSO$_2$, J=15.0 Hz, J=1.0 Hz); 6.6 (1H, dd, CH=CHSO$_2$, J=15.0 Hz, J=6.5 Hz).

$^{13}$C-NMR (d, DEPT, CDCl$_3$): 22.701 (CH$_2$, 55%); 23.536 (CH$_2$, 45%); 28.220 ([CH$_3$]$_3$); 30.369 (CH$_2$, 45%); 31.487 (CH$_2$, 55%); 43.733 (CH$_2$CO); 46.168 (CH$_2$, 55%); 46.542 (CH$_2$, 45%); 52.478 (OCH$_3$); 56.821 (CH); 127.032 (CH=, 55%); 127.478 (CH, 45%); 145.203 (CH=, 55%); 145.631 (CH=, 45%).

To the solution of (VI) converted into the corresponding sulfonil chloride (133 mg, 0.447 mmol) in CH$_2$Cl$_2$ (4.47 ml), under nitrogen, (XXVII) deprotected and converted into the corresponding hydrochloride salt, (84.85 mg, 0.298 mmol), DBU (90.6 mg, 0.596 mmol, 88.6 μl) and DMAP (7.28 mg, 0.0596 mmol) in CH$_2$Cl$_2$ (2 ml) were added. After 1 h phosphate buffer (5 ml) was added; the aqueous phase was extracted with CH$_2$Cl$_2$, the organic extracts were collected, dried (Na$_2$SO$_4$) and evaporated to give a crude mixture which was purified by flash chromatography (n-hexane/AcOEt=40/60) to give product (XXVIII) in 41% yield.

$^1$H-NMR (d, CDCl$_3$): 0.96 (6H, dd, (CH$_3$)$_2$CH, J=1.2 Hz, J=6.7 Hz); 1.44 (9H, s, [CH$_3$]$_3$C); 1.83–1.95 (4H, m, NCHCHHCH$_2$+(CH$_3$)$_2$CH); 2.02–2.15 (1H, m, NCHCHH); 3.3–3.4 (2H, m, NCHCH$_2$CH$_2$CH$_2$); 5.76 (3H, s, OCH$_3$); 5.87 (2H, d, NHCH$_2$CO, J=5.5 Hz); 4.08–4.18 (1H, m, (CH₃)₂CHCH); 4.26–4.30 (1H, m, NCH); 4.75 (1H, d, BOCNH, J=8.2 Hz); 5.44 (1H, t, NHCH₂CO, J=5.1 Hz); 6.27 (1H, CH=CHSO₂, J=15.1 Hz); 6.46 (1H, d, CH=CHSO₂, J=14.97); 6.66 (2H, dd, 2×CH=CHSO₂, J=5.5 Hz, J=14.7 Hz).

¹³C-NMR (d, CDCl₃): 18.176 (CH₃); 18.769 (CH₃); 23.927 (CH₂); 28.173 ([CH₃]₃); 31.549 (CH); 31.858 (CH₂); 43.835 (CH₂); 48.712 (CH₂); 52.579 (OCH₃); 56.695 (CH); 59.157 (CH); 124.999 (CH=); 128.911 (CH=); 144.349 (CH=); 145.616 (CH=).

Likewise, the following products were prepared:

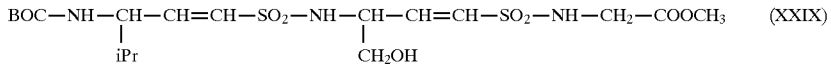
(XXIX)

¹H-NMR (d, CDCl₃): 0.97 (3H, d, CH₃CH, J=6.7 Hz); 0.97 (3H, d, CH₃CH, J=6.9 Hz); 1.46 (9H, s, [CH₃]₃C); 1.85 (1H, m, Me₂CH); 3.52 (1H, dd, CHHOH, J=6.7 Hz, J=11.7 Hz); 3.78 (3H, s, OCH₃); 3.84 (1H, dd, CHHOH, J=3.8 Hz, J=11.7 Hz); 3.91 (2H, d, CH₂COO, J=5.87 Hz); 3.9–4.1 (2H, m, 2×CHN); 4.88 (1H, d, NH, J=7.5 Hz); 5.42 (1H, d, NH, J=6.9 Hz); 5.78 (1H, t, NHCH₂, J=5.8 Hz); 6.39 (1H, d, CH=CHSO₂, J=15 Hz); 6.57 (1H, dd, CH=CHSO₂, J=6.6 Hz, J=15 Hz); 6.65 (2H, s, CH=CHSO₂).

¹³C-NMR (d, DEPT, CDCl₃): 18.367 (CH₃); 18.650 (CH₃); 28.220 ([CH₃]₃); 31.446 (Me₂CH); 43.937 (CH₂COO); 52.681 (OCH₃); 55.863 (CHN); 57.177 (CHN); 63.418 (CH₂OH); 129.494 (CH=); 131.063 (CH=); 140.513 (CH=); 143.942 (CH=).

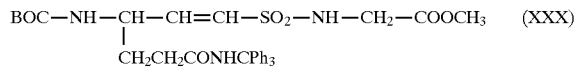
(XXX)

¹H-NMR (d, CDCl₃): 1.45 (9H, s, [CH₃]₃C); 1.5–2.0 (2H, m, CH₂CH₂CO); 2.45 (2H, t, CH₂CH₂CO, J=7.8 Hz); 3.75 (3H, s, OCH₃); 3.9 (2H, t, NHCH₂COO, J=3.48 Hz); 4.4 (1H, broad, NHCH); 5.2 (1H, broad, BOCNH); 6.3 (1H, d, CH=CHSO₂, J=15.2 Hz); 6.65 (1H, dd, CH=CHSO₂, J=15.2 Hz; J=5.2 Hz); 6.85 (1H, s, NHCPh₃); 7.15–7.4 (15H, m, ArH)

EXAMPLE 10

The following methanesulfonyl derivatives were in addition prepared by reaction of the corresponding amine chloridrates with methanesulfonyl chloride:

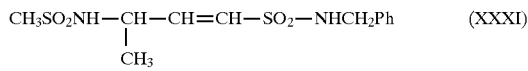
(XXXI)

obtained in 70% yield.

¹H-NMR (d, CDCl₃): 1.34 (3H, d, CH₃CH, J=7.1 Hz); 2.96 (3H, s, CH₃SO₂); 4.23 (3H, d, NCH₂Ph+NHCH, J=6.1 Hz); 4.74 (1H, d, MeSO₂NH, J=8.3 Hz); 5.01 (1H, t, SO₂NHBn, J=6.1 Hz); 6.38 (1H, dd, CH=CHSO₂, J=1.6 Hz, J=15.1 Hz); 6.66 (1H, dd, CH=CHSO₂, J=5 Hz, J=15.1 Hz); 7.35 (5H, m, ArH).

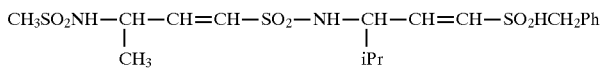
(XXXII)

obtained in 83% yield.

¹H-NMR (d, CDCl₃): 0.897 (3H, d, CH₃, J=3.2 Hz); 0.98 (3H, d, CH₃, J=3.2 Hz); 1.35 (3H, d, CH₃, J=6.5 Hz); 1.85 (1H, m, CH(CH₃)₂); 2.95 (3H, s, CH₃SO₂); 3.85 (1H, m, CHCH(CH₃)₂); 4.15 (3H, m, CHCH₃+CH₂); 5.5 (3H, m, 3×NH); 6.4 (1H, d, CH(iPr)CH=CHSO₂, J=15 Hz); 6.45 (1H, d, CH(CH₃)CH=CHSO₂, J=14.2 Hz); 6.55 (1H, d, CH(iPr)CH=CHSO₂, J=15 Hz); 6.65 (1H, dd, CH(CH₃)CH=CHSO₂, J=4.48 Hz, J=14.2 Hz).

We claim:

1. A derivative of an aminosulfonic acid, having the formula I:

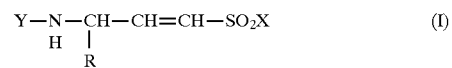
(I)

where:
R is chosen among: hydrogen, a fragment corresponding to the side chain of a natural aminoacid, a substituted or unsubstituted, linear, branched or cyclic alkyl group, arylalkyl group, an aryl group, and a heteroaromatic group;

Y indicates hydrogen, and the saline forms of the corresponding amine, or any protective group commonly utilized for the protection of the amine group;

X indicates Cl, OH, OCH₂CH₃, OCH₃, ONBu₄, NHCH₂Ph, provided that: when Y is chosen among PhCH₂CO, (CH₃)₃COCO, and X is chosen among OCH-CH, ONBu₄ or when Y is chosen as PhOCH₂CO and X is chosen as OCH₂CH₃ or when Y is hydrogen or a saline form of the corresponding amine and

X is chosen as OH,

R is different from CH₃.

2. The aminosulfonic acid derivative according to claim 1, wherein R is —CH₃, Y is the (CH₃)₃C—OCO-protective group and X is Cl.

3. A derivative of an aminosulfonic acid, according to claim 1, wherein R is chosen among the side chains of the proteinogenic aminoacids, Y is the (CH₃)₃C—OCO— protective group, X is OR₁, where R₁ is chosen among —CH₃ and —CH₃CH₃, according to formula II:

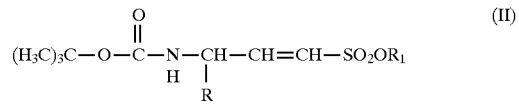
(II)

provided that:

when R₁ is —CH₃CH₃, R is different from CH₃.

4. The aminosulfonic acid derivative, having the formula I:

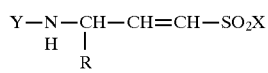

where
  Y is hydrogen and the amine is in the form of the hydrochloride salt, R is $CH_3$ and X is $OCH_2CH_3$.

5. The aminosulfonic acid derivative according to formula II:

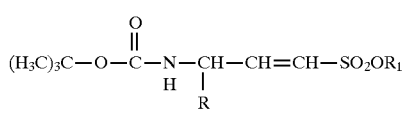

wherein R is $(CH_3)_2CH-$, and where $R_1$ is $-CH_2CH_3$.

6. The aminosulfonic acid derivative according to the formula II:
  wherein R is $CH_3$, and where $R_1$ is $CH_3$.

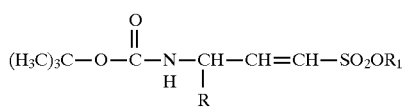

7. An aminosulfonic acid derivative, having the following chemical formulae:

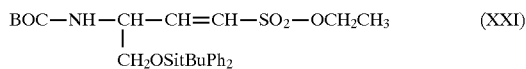

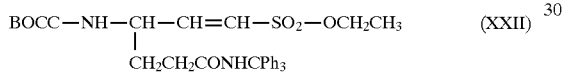

8. An aminosulfonic acid derivative having the following chemical formula:

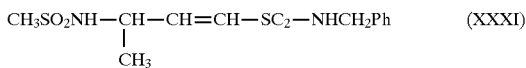

9. A process for the preparation of derivatives of aminosulfonic acids, said derivatives of aminosulfonic acids having the formula I:

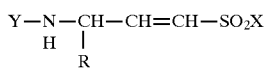

where
  R is chosen among: hydrogen, a fragment corresponding to the side chain of natural aminoacid, a substituted or unsubstituted, linear, branched or cyclic alkyl group, arylalkyl group, an aryl group and a heteroaromatic group;
  Y indicates hydrogen, and the saline forms of the corresponding amine, or any protective group commonly utilized for the protection of the amine group;
  X indicates Cl, OH, $OCH_3CH_3$, $OCH_3$, $ONBu_4$, $NHCH_3Ph$,
  provided that: when Y is chosen among $PhCH_2CO$, $(CH_3)_3COCO$, and X is chosen among $OCH_2CH_3$, $ONBu_4$
  or
  when Y is chosen as $PhOCH_2CO$ and X is chosen as $OCH_2CH_3$
  or
  when Y is hydrogen or a saline form of the corresponding amine and
  X is chosen as OH,
  R is different from $CH_3$;
  said process comprising the steps of
    converting a natural alpha-aminoacid into an alpha-aminoaldehyde; and
    converting said alpha-aminoaldehyde into said derivative of aminosulfonic acid by means of Wittig-Horner's reaction.

10. The process for the preparation of derivatives of aminosulfonic acids according to claim 9, wherein said natural alpha-aminoacids are proteinogenic aminoacids either in (L) form or in (D) form.

* * * * *